US010945682B2

(12) United States Patent
Cant et al.

(10) Patent No.: US 10,945,682 B2
(45) Date of Patent: Mar. 16, 2021

(54) GEOMETRIC MISALIGNMENT CORRECTION METHOD FOR CHEST TOMOSYNTHESIS RECONSTRUCTION (71) Applicant: Agfa Healthcare NV, Mortsel (BE)

(72) Inventors: Jeroen Cant, Mortsel (BE); Jan Sijbers, Mortsel (BE)

(73) Assignee: AGFA HEALTHCARE NV, Mortsel (BE)

(*) Notice: Subject to any disclaimer, the term of this patent is extended or adjusted under 35 U.S.C. 154(b) by 141 days.

(21) Appl. No.: 16/308,303

(22) PCT Filed: Jun. 8, 2017

(86) PCT No.: PCT/EP2017/063989
§ 371 (c)(1),
(2) Date: Dec. 7, 2018

(87) PCT Pub. No.: WO2017/211968
PCT Pub. Date: Dec. 14, 2017

(65) Prior Publication Data
US 2019/0216408 A1 Jul. 18, 2019

(30) Foreign Application Priority Data
Jun. 9, 2016 (EP) .................................... 16173767

(51) Int. Cl.
*A61B 6/02* (2006.01)
*A61B 6/00* (2006.01)
(Continued)

(52) U.S. Cl.
CPC ............ *A61B 6/025* (2013.01); *A61B 6/5205* (2013.01); *A61B 6/587* (2013.01); *G06T 11/005* (2013.01);
(Continued)

(58) Field of Classification Search
CPC ......... A61B 6/025; A61B 6/583; A61B 6/587; A61B 6/5205; A61B 5/0073; G06T 11/005; G01N 2015/1445; G16H 30/40
(Continued)

(56) References Cited

U.S. PATENT DOCUMENTS

2006/0045235 A1  3/2006 Bruder et al.

FOREIGN PATENT DOCUMENTS

| DE | 10 2013 200 329 A1 | 7/2014 |
| EP | 2 490 180 A1 | 8/2012 |
| WO | 2014/108237 A1 | 7/2014 |

OTHER PUBLICATIONS

Zhang, et al. (Artifact reduction methods for truncated projections in iterative breast tomosynthesis reconstruction), pp. 1-21. (Year: 2009).*

(Continued)

*Primary Examiner* — Daniel G Mariam
(74) *Attorney, Agent, or Firm* — Stinson LLP (57) ABSTRACT A method and system to correct for alignment errors between assumed and actual geometric parameters of an acquisition geometry during image reconstruction in a chest tomosynthesis application includes receiving at least 2 raw projection images acquired on at least 2 different positions in a known acquisition geometry, determining an actual geometric parameter value by determining the minimum of a redundant planes cost function which is calculated for a varying range of the geometric parameter values, and which is determined by: a) at least one plane which intersects an X-ray source trajectory with at least two points, b) an intersection between the planes and a detector surface for which points the source positions are determined, and c) for which the parameters determining the intersection ($\lambda$, $\mu$, l) are used for the construction of the cost function, applying the calculated actual geometric parameter value of the (Continued)

acquisition geometry for the image reconstruction of the plurality of images, characterized in that, a weighting function is applied to the plurality of acquired images prior to calculating the cost function.

15 Claims, 6 Drawing Sheets

(51) Int. Cl.
  *G06T 11/00* (2006.01)
  *G16H 30/40* (2018.01)
(52) U.S. Cl.
  CPC ........ *G06T 2211/416* (2013.01); *G16H 30/40* (2018.01)
(58) Field of Classification Search
  USPC .......................................................... 382/132
  See application file for complete search history.

(56) References Cited

OTHER PUBLICATIONS

Kunze, et al. (Iterative Extended Field of View Reconstruction), pp. 1-12. (Year: 2007).*

Computer English Translation of WO-2014/108237. (Year: 2014).*

Official Communication issued in International Patent Application No. PCT/EP2017/063989, dated Oct. 6, 2017.

Debbeler et al., "A New CT Rawdata Redundancy Measure applied to Automated Misalignment Correction", The 12th International Meeting on Fully Three-Dimensional Image Reconstruction in Radiology and Nuclear Medicine, 2013, pp. 264-267.

Dobbins, III et al., "Digital Tomosynthesis of the Chest", Journal of Thoracic Imaging, vol. 23, No. 2, May 2008, pp. 86-92.

Molk et al., "Digital tomosynthesis of the chest: A literature review", Radiography, vol. 21, No. 2, 2015, pp. 197-202.

Miao et al., "A phantom-based calibration method for digital x-ray tomosynthesis", J Xray Sci Technol., vol. 20, No. 1, Jan. 2012, pp. 17-29.

Han et al., "A novel fully automatic scheme for fiducial marker-based alignment in electron tomography", Journal of Structural Biology, vol. 192, No. 3, Dec. 2015, pp. 403-417.

Grulich et al., "Geometric Adjustment of X-ray Tomosynthesis", The 13th International Meeting on Fully Three-Dimensional Image Reconstruction in Radiology and Nuclear Medicine, 2015, pp. 468-471.

* cited by examiner

GEOMETRIC MISALIGNMENT CORRECTION METHOD FOR CHEST TOMOSYNTHESIS RECONSTRUCTION

CROSS REFERENCE TO RELATED APPLICATIONS

This application is a 371 National Stage Application of PCT/EP2017/063989, filed Jun. 8, 2017. This application claims the benefit of European Application No. 16173767.1, filed Jun. 9, 2016, which is incorporated by reference herein in its entirety.

BACKGROUND OF THE INVENTION

1. Field of the Invention

The present invention relates generally to the correction of errors in the assumed acquisition geometry of a chest tomosynthesis X-ray system, in order to reduce the occurrence of reconstruction image artefacts during image reconstruction.

2. Description of the Related Art

In medical imaging, chest tomosynthesis (TS) is a form of limited angle X-ray tomography with which 3D images of a patient can be computed. In chest tomosynthesis, projection images are acquired using a fixed flat panel detector, which is placed behind the patient and a motorized X-ray tube, typically moving on a straight line, to create projection images from a limited angle. An intrinsic characteristic of chest imaging and chest tomography is that the imaged body part—the chest—appears 'truncated' in the projection images. Nevertheless, other applications may be envisaged in different clinical or non-clinical application domains, but showing the same image acquisition constraints (namely truncation).

Subsequently, a reconstruction algorithm is used to reconstruct section planes parallel to the detector. With slight modifications such as X-ray tube motorization and flat panel detector synchronization, chest TS can be performed on standard X-ray modalities. Chest TS offers a high in-plane resolution but suffers from a low depth resolution due to the limited acquisition angle of the projection images (as described in J. T. Dobbins, H. P. McAdams, D. J. Godfrey, and C. M. Li, "Digital tomosynthesis of the chest," Journal of Thoracic Imaging, vol. 23, no. 2, pp. 86-92, 2008.).

Nevertheless, chest TS is capable of separating overlapping anatomy into subsequent section planes, making the detection of certain pathologies easier compared to standard X-ray images (refer to N. Molk and E. Seeram, "Digital tomosynthesis of the chest: A literature review," Radiography, vol. 21, no. 2, pp. 197-202, 2015.).

In order to reconstruct high quality TS images, accurate knowledge of the relative positions of the X-ray source and detector is crucial. Inaccuracies in the assumed acquisition geometry lead to reconstruction artefacts such as striping and blurring. For chest tomosynthesis, an important geometric parameter is the orientation of the detector relative to the linear motion path of the X-ray tube. Even inaccuracies smaller than 0.5° on the detector orientation may lead to significant image reconstruction artefacts.

When acquisitions are performed with a rectangular detector in a table, these inaccuracies cannot be easily avoided as the mechanical detector assembly is allowed to be rotated 90° by the operator, resulting in inaccurate orientation due to mechanical limitations of the locking mechanism of the assembly itself. Moreover in case of mobile tomosynthesis, the detector orientation is even more difficult to control as there is no mechanical alignment or coupling between the X-ray source trajectory and the detector angle.

Therefore, methods are needed to accurately calibrate the acquisition geometry. The acquisition geometry can be measured offline (meaning not during an acquisition), using a calibration phantom (as for instance described by: H. Miao, X. Wu, H. Zhao, and H. Liu, "A phantom-based calibration method for digital x-ray tomosynthesis." J. Xray. Sci. Technol., vol. 20, no. 1, pp. 17-29, jan 2012.), and online using the projection images.

For online calibration, radio opaque markers can be used to derive the acquisition geometry (see R. Han, L. Wang, Z. Liu, F. Sun, and F. Zhang, "A novel fully automatic scheme for fiducial marker-based alignment in electron tomography." J. Struct. Biol., vol. 192, no. 3, pp. 403-17, dec 2015., or see as well U.S. Pat. No. 8,000,522), but this method is cumbersome since the markers need to be applied very accurately prior to each acquisition.

Another way is to exploit data consistency conditions, which describe redundancies between projection images. From these conditions, a cost function can be formulated that, after minimization, leads to the optimal geometric parameters such as detector orientation and position. Such a technique was developed for estimating and correcting the geometric parameters in a cone beam computed tomography setup, based on epipolar consistency conditions (ECC) (see C. Debbeler, N. Maass, M. Elter, F. Dennerlein, and T. M. Buzug, "A New CT Rawdata Redundancy Measure applied to Automated Misalignment Correction," Proc. Fully Three-dimensional Image Reconstr. Radiol. Nucl. Med., pp. 264-267, 2013.). The same technique is disclosed in a patent application WO2014/108237.

However, improvements are necessary for tomosynthesis, as the ECC are not robust enough to deal with truncated projections. In recent scientific work, a heuristic weighting function was introduced to weigh the gray values in the projection images, depending on the fraction of the ray passing the part of the object that is visible on all projections and an estimation of the maximal object thickness (see A. Grulich, Tobias and Holub, Wolfgang and Hassler, Ulf and Aichert, André and Maier, "Geometric Adjustment of X-ray Tomosynthesis," in Fully Three-Dimensional Image Reconstr. Radiol. Nucl. Med., Newport, 2015, pp. 468-471.). This described method thus describes a weighting method which relies on the estimated patient size (thickness) which is not convenient to provide good results.

SUMMARY OF THE INVENTION

The present invention provides a method and system for chest tomosynthesis, comprising a method to improve the robustness of the calculation method used to correct for discrepancies between the assumed acquisition geometry and the actual acquisition geometry of a tomosynthesis image acquisition, as set out below. It should be noted that this invention is not limited to the application in chest tomosynthesis only, and that other applications may be envisaged in different clinical or non-clinical application domains, where the same image acquisition constraints are encountered (namely truncation).

The above-described aspects are solved by a system as set out below.

In the context of this invention, an acquisition geometry has to be understood as the geometric arrangement of the different components making up a digital imaging modality, being the geometric setup defined in terms of a set of geometric parameters of the arrangement of the components of a so-called image acquisition unit. In order to be functional, the acquisition geometry for a tomosynthesis imaging needs to be accurately known for the reconstruction algorithm to work properly. However, the real acquisition geometry may deviate slightly from the assumed acquisition geometry which is the theoretical setup of the acquisition geometry. A data acquisition unit has to be understood as the configuration of components to perform an X-ray image acquisition, commonly named an X-ray modality.

The components making up such a system are typically a patient positioning device, an X-ray source and a digital image detector. The patient positioning device is required to position the patient or object in a stable and accessible way (such as a table, or different positioning unit) for the X-ray source and digital image detector. The positioning device is however a recommended, but optional component for a chest tomosynthesis system; the patient may also be positioned while standing freely close to the digital image detector.

The X-ray source typically is an X-ray tube mounted on a stand or mount, and is driven by an X-ray generator supplying the high voltage current to the tube filament at the moment of exposure. The digital image detector acquires the X-ray shadow of the imaged patient or object casted by the X-rays originating from the X-ray source. The projection image is acquired and converted into a digitally readable format. This digitally readable image is called in the context of this application a raw projection image as it comprises the raw or unprocessed image data from a single projection image acquisition.

The projection images of an object are acquired in different positions, meaning that in most cases the object is kept immobilized while either the X-ray source, or the digital image detector (or both) is moved to a different position before acquiring a subsequent projection image. In most cases, the X-ray detector and/or the image detector describe a geometrical trajectory such as a circular or linear path with respect to a fixed reference point in the acquisition geometry or to each other. The acquisition geometry describes this relation between X-ray source, image detector and imaged object for subsequent acquisitions. In chest tomosynthesis acquisitions, mostly only the X-ray source is moved along a linear path on which at fixed intervals the movement of the X-ray source is interrupted and acquisitions are made of the imaged object. The total angle covered by the X-ray source between the first and last acquisition of as seen from the detector is between 5 and 15°.

A data processing unit subsequently performs various processing tasks on the projection images that have been transferred from the data acquisition unit. For example, the processing unit performs on the projection images desired operations including data sampling, data shifting, filtering, selection and reconstruction. The processing unit calculates reconstructed images based on the projection images. As will be described later in greater detail, the processing unit performs certain filtering operations on the projection images before or after reconstruction.

The functions of the data processing unit can be implemented on a computer system, and as such the present invention can be implemented as a computer program product adapted to carry out the steps set out in the description. The computer executable program code adapted to carry out the steps set out in the description can be stored on a computer readable medium.

Specific examples and preferred embodiments are set out below.

The present invention is beneficial in that the correction method is capable to correct for discrepancies between the assumed and actual acquisition geometry during reconstruction of a truncated tomosynthesis image data set, and this without the need for upfront calibration of the tomosynthesis X-ray system. The correction method improves the robustness of the reconstruction method, and prevents the appearance of reconstruction artefacts in the resulting reconstructed image.

Further advantages and embodiments of the present invention will become apparent from the following description and drawings.

DETAILED DESCRIPTION OF THE PREFERRED EMBODIMENTS

In the following detailed description, reference is made in sufficient detail to the above referenced drawings, allowing those skilled in the art to practice the embodiments explained below.

Embodiments of the present invention provide a system and a method for acquiring and reconstructing a chest tomosynthesis projection image data set. The method disclosed by this invention is based on the original method of Debbeler (already referred to above), and is a modification of this method to improve the robustness against truncation.

Figure 1:
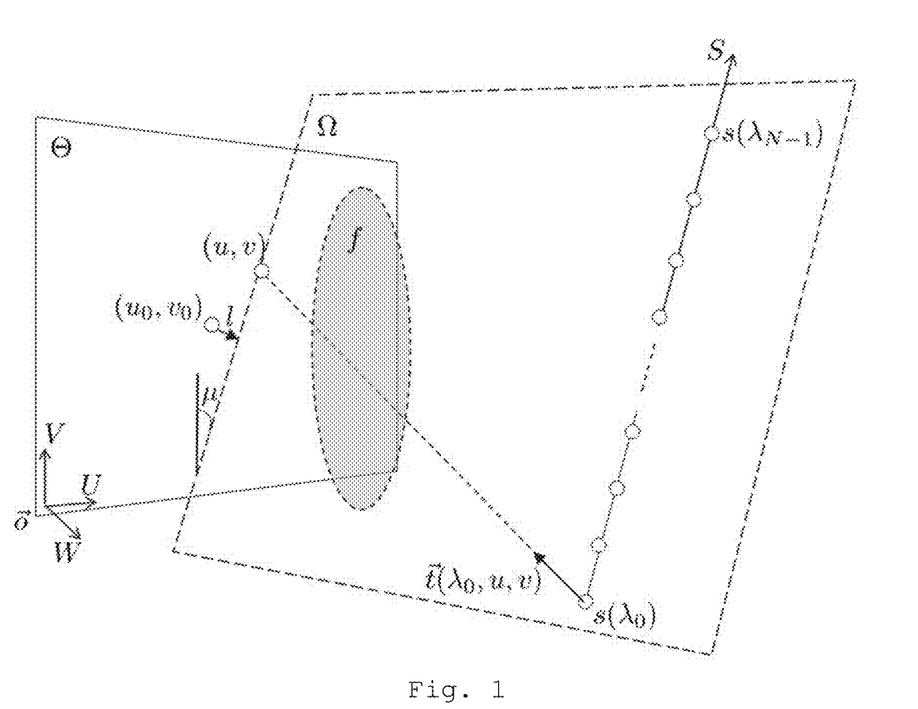
FIG. 1 illustrates the geometric setup of a chest tomosynthesis acquisition in one embodiment of the invention. N X-ray images are acquired on a stationary flat panel θ with an X-ray tube that moves on a straight line S. The angle μ represents the orientation of the digital image detector relative to the X-ray source path. Most chest tomosynthesis systems are designed so that μ=0.

A schematic representation of chest tomosynthesis is illustrated in FIG. 1. Projections are acquired of a patient f with a stationary detector θ. The N subsequent positions of the X-ray source are indicated as s($\lambda_i$). In one embodiment of the invention, the X-ray source moves on a linear path S. In other embodiments of this invention, the source might move on a circular path over a limited angle.

The detailed description given here will further focus on the first embodiment in which the source moves on a linear path. The coordinate frame attached to the detector has axes (U, V, W).

The epipolar redundancy criterion describes the following relationship between two projection images. For two source points s($\lambda_n$) and s($\lambda_{n'}$), multiple planes Ω can be drawn that intersect both points and the detector along an intersection which can be parameterized by an angle μ and a distance l from the detector center ($u_0$, $v_0$). For noiseless acquisitions and without truncation, it can be proven that $$g_3(\lambda_n, \mu, l) = g_3(\lambda_{n'}, \mu, l) \quad (1)$$

with $g_3$ defined as:

$$g_3(\lambda_n, \mu, l) = \frac{\partial}{\partial l} g_2(\lambda_n, \mu, l) \quad (2)$$

where $$g_2(\lambda_n, \mu, l) = \int_{-\infty}^{\infty} g_1(\lambda_n, l\cos\mu - t\sin\mu, l\sin\mu + t\cos\mu) dt \quad (3)$$

and $$g_1(\lambda_n, u, v) = \frac{1}{|w \cdot t(\lambda_n, u, v)|} p(\lambda_n, u, v) \quad (4)$$

with p the projection data, w the normal of the detector and t(n,u,v) the direction of the ray arriving in detector pixel (u, v) of the $n^{th}$ projection. Based on this, a redundant cost planes function $C_{RP}$ can be derived which reaches a minimum if the geometric parameters (and hence λ and l) are correctly estimated:

$$C_{RP} = \sqrt{\sum_{n=0}^{N-1} \sum_{\mu=-\pi/2}^{\pi/2} \sum_{l=-L_{max}}^{L_{max}} (g_3(\lambda_n, \mu, l) - g_3(\lambda_{n'}, \mu, l))^2}$$

Although that other geometric parameters may be optimized to achieve a minimum in the cost planes function $C_{RP}$, a first embodiment of this invention optimizes the detector orientation μ, relative to the linear motion path of the X-ray tube.

More specifically in chest tomosynthesis, substantial truncation of the object is present in the projections both in the horizontal and vertical direction. In the case of even very small angle deviations p it can be expected that the largest inconsistencies between the projections are found at the top and bottom regions of the projections, as certain parts of the patient will not be imaged in this case, depending on the acquisition angle of the tube. Intuitively, the horizontal truncation would cause fewer inconsistencies. While in the prior art it has been attempted to optimize the efficiency of the cost function calculation by applying a weighting function to reduce the weight in the cost function of pixels that were suspected to contain information that was not present in all projections (see A. Grulich, Tobias and Holub, Wolfgang and Hassler, Ulf and Aichert, André and Maier, "Geometric Adjustment of X-ray Tomosynthesis," in Fully Three-Dimensional Image Reconstr. Radiol. Nucl. Med., Newport, 2015, pp. 468-471.), the invention described in this application proposes a different approach.

The equation above (3) is very sensitive for pixels near the upright (horizontal) image edges, even if an object would have been imaged that fitted perfectly on the detector without horizontal truncation. A small deviation from 0 in μ would cause a large part of the image pixels in the image border to fall off the intersection with the plane Ω, causing a large discontinuity in $g_3$ and thus making the entire cost function $C_{RP}$ unstable.

Therefore, in order to reduce the impact of pixels near the edge of the projections on the cost function and in a specific embodiment of this invention, a specific weighting function is applied. In the regions of relative width $L_1$ and $R_1$, weights are increased from 0 to 1 according to a Gaussian distribution with $L_1=3\sigma$ and respectively $R_1=3\sigma$. See FIG. 2.

In another embodiment, the same filter is also disclosed to compensate for vertical truncation.

Figure 2:
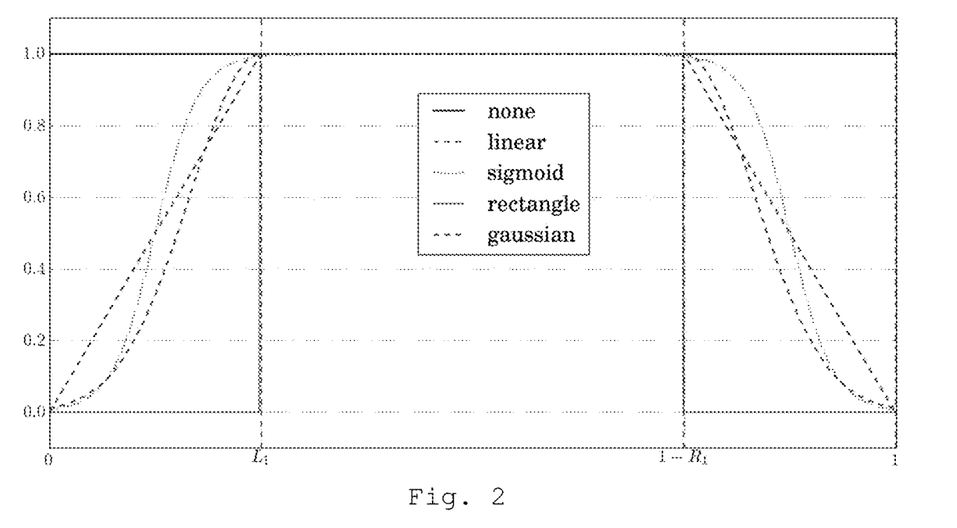
FIG. 2 shows the shapes of different proposed weighting functions which may be applied to the projection image prior to or after calculating the redundant cost planes function $C_{RP}$.

In yet other embodiments, different shapes of weighting curves are proposed, such as linear, rectangular or sigmoid shaped sighting curves (such as depicted in FIG. 2).

The above has been confirmed by a simulated chest tomosynthesis exam experiment using the XCAT phantom as the imaged object. A set of 11 simulated projections was generated using a mathematical (computer) toolkit with a source-image distance of 120 cm and linear tube motion path of 20 cm. Detector size was set to 360×420 pixels of 1 mm size. The detector was placed at a relative rotation of 10° with the motion path of the X-ray tube. Experiments were performed to estimate this simulated detector rotation, through the calculation of the said redundant cost planes functions.

The maximum achievable accuracy of the estimation of the detector rotation is related to the detector size; the maximum accuracy Δ is defined as the angle increment for which a rays passes through a neighbouring pixel at the edge of the image: $\Delta=\tan^{-1}(1/210)=0.27°$.

Figure 3:
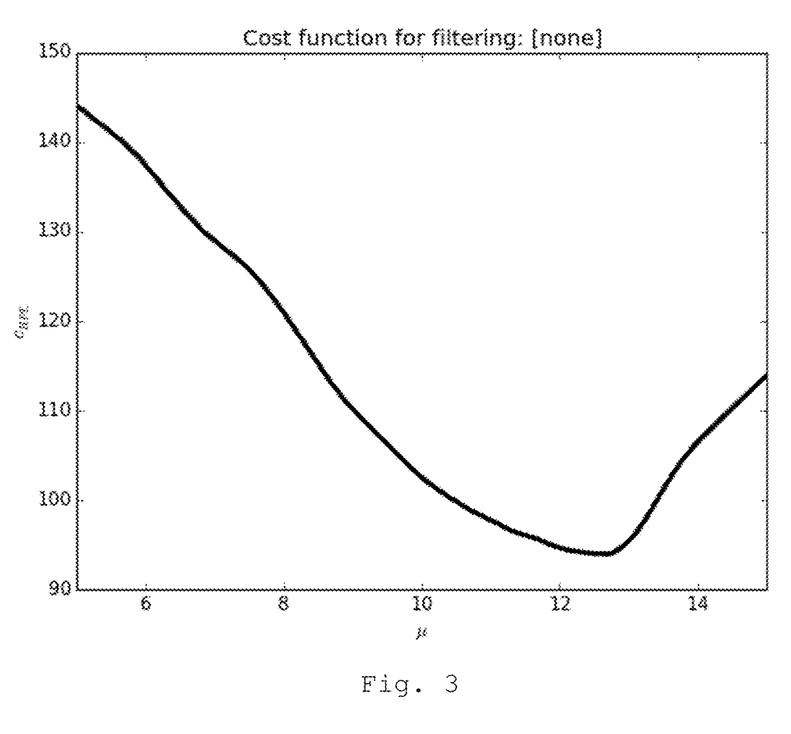
FIG. 3 shows the shape of cost function $C_{RP}$ for estimated digital image detector angle μ without truncation filtering applied first. The cost function is calculated for a simulated chest tomosynthesis exam using the XCAT phantom.

FIG. 3 clearly shows that the estimation of the orientation angle, based on the uncorrected raw projection images results in the estimation of μ=12.7° as the correct angle. As can be seen in FIG. 3, the cost function $C_{RP}$ achieved a minimum value at 12.7° which is however well above the 'true' angle of 10°.

Figure 4:
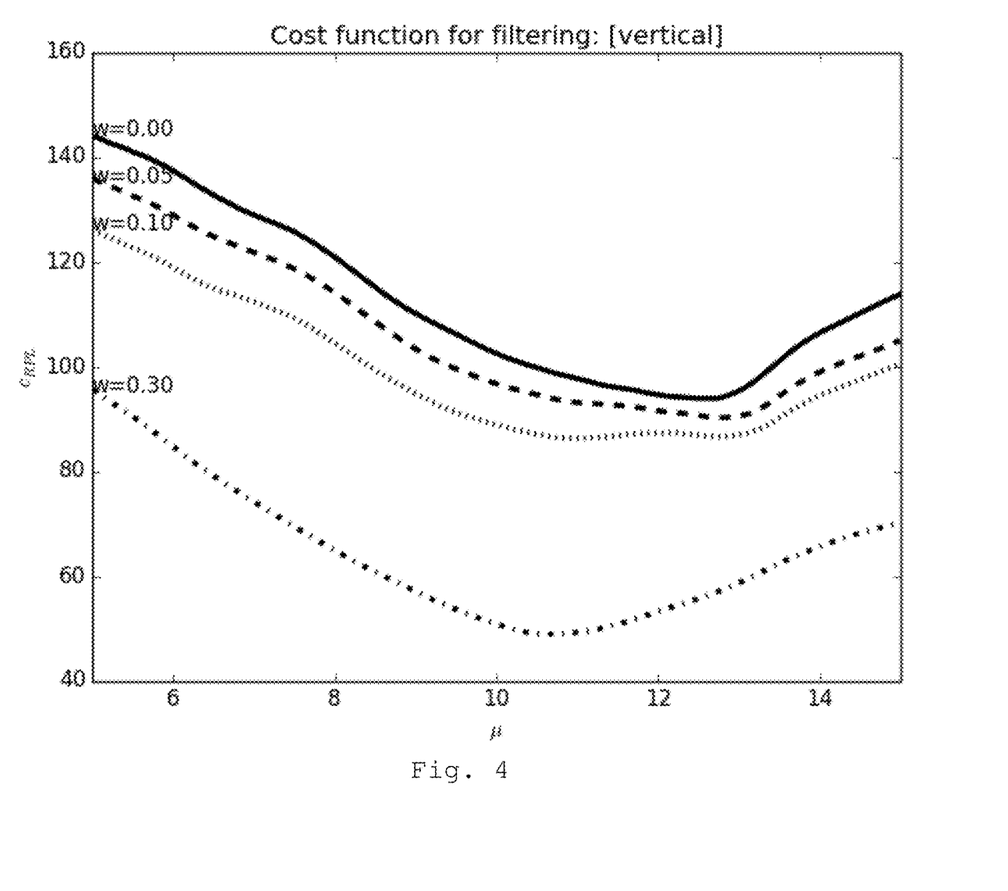
FIG. 4 shows the shape of different cost functions calculated for the same simulated chest tomosynthesis exam. Vertical Gaussian truncation filters where used with varying values of $w=L_1=L_2$.
Figure 5:
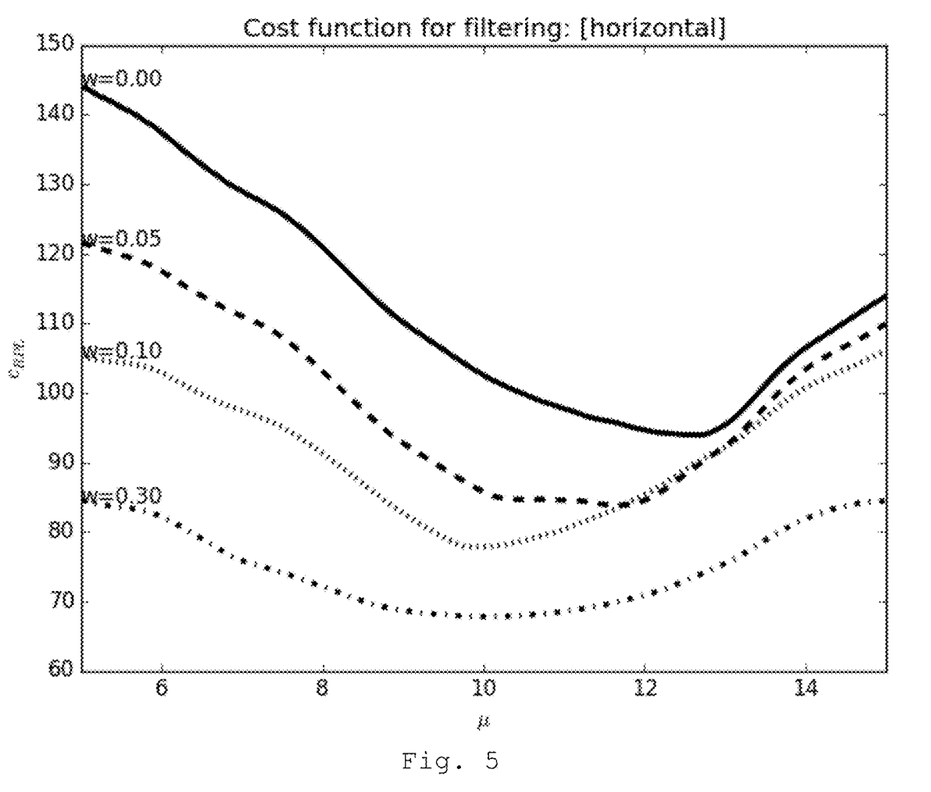
FIG. 5 shows the shape of different cost functions calculated for the same simulated chest tomosynthesis exam. Horizontal Gaussian truncation filters where used with varying values of $w=L_1=L_2$.
Figure 6:
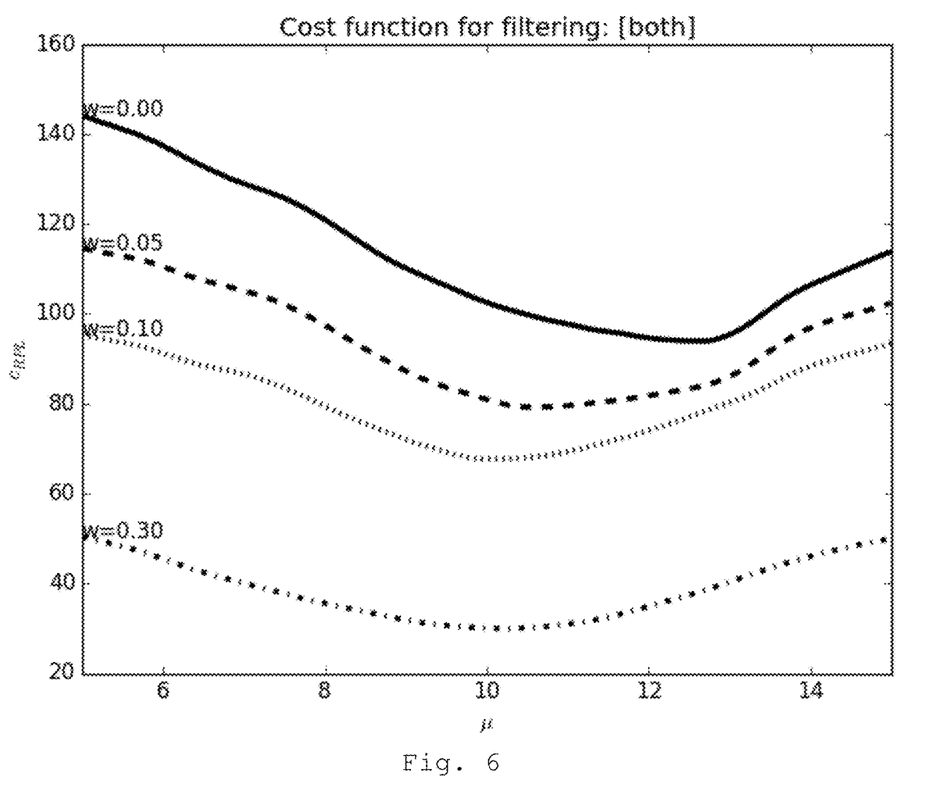
FIG. 6 shows the shape of different cost functions calculated for the same simulated chest tomosynthesis exam. Gaussian truncation filters where used in both horizontal and vertical direction. The calculated results for the disclosed experimental setup show that the cost function reaches a minimum around an angle correction of about 13° in case that filters with w<0.01 are chosen. The correct result (around 10°) prominently appears as the minima of the different cost functions calculated with values w>0.05.

FIGS. 4 and 5 show similar calculations of the detector rotation, but here the different cost function curves are calculated based on the same set of projection images, but where respectively vertical and horizontal Gaussian truncation filters with varying values of $w=L_1=L_2$ where applied before the reconstruction. Surprisingly, when the applied filter widths are w>0.10, the minimum of $C_{RP}$ moves towards 10°. When w is further increased beyond 0.40, the calculations show that the value of μ no longer is estimated correctly, which is not a surprise since the amount of useable image data is dramatically reduced and potentially no longer representative. Combining both horizontal and vertical filters (FIG. 6) more or less produces the same results, confirming the need for horizontal filtering despite the mainly vertical truncation inconsistencies.

In another embodiment, the same weighting functions are applied, but as opposed to the previous embodiment, to the calculated cost functions themselves (without applying the weighting functions to the projection images). This method is supported by the fact that the calculation of the weighting functions out of the different projection images is a mathematically linear operation.

The invention claimed is:

1. A method to correct for alignment errors between assumed and actual geometric parameters of an acquisition geometry during image reconstruction in a tomosynthesis application, the method comprising the steps of:
receiving at least two projection images acquired at least two different positions in a known acquisition geometry;
applying a weighting function to the at least two projection images;
after applying the weighting function, determining a minimum of a redundant planes cost function for the at least two projection images, which is calculated for a varying range of geometric parameter values, and which is determined by:
a) planes each of which intersects an X-ray source trajectory at at least two points;
b) intersection points between the planes and a detector surface for which source positions are determined; and
c) for which parameters determining the intersection points are used for construction of the redundant planes cost function;
calculating an actual geometric parameter value based on the determined minimum of the redundant planes cost function; and
applying the calculated actual geometric parameter value of the acquisition geometry for the image reconstruction of the at least two projection images.

2. The method according to claim 1, wherein the calculated actual geometric parameter of the acquisition geometry is an angle between an actual orientation of an image detector relative to one of the planes that intersects with the at least two points defining the X-ray source trajectory in an imaging modality.

3. The method according to claim 1, wherein the weighting function is a Gaussian function, and weights of pixel values, or redundant cost function values, are increased from 0 to 1 according to a Gaussian distribution in which $3\sigma=L_1$ and $3\sigma=R_1$, and $L_1$ and $R_1$ are relative widths of an applied truncation filter.

4. The method according to claim 1, wherein the weighting function is a sigmoid function, and weights of pixel values, or respectively redundant cost function values, are increased from 0 to 1 according to a sigmoid distribution between 0 and $L_1$ and between $R_1$ and 0, in which $L_1$ and $R_1$ are relative widths of an applied truncation filter.

5. The method according to claim 1, wherein the weighting function is a linear function, and weights of pixel values, or respectively redundant cost function values, are increased from 0 to 1 according to a linear distribution between 0 and $L_1$, and between $R_1$ and 0, in which $L_1$ and $R_1$ are relative widths of an applied truncation filter.

6. A medical imaging apparatus for a tomosynthesis application, the medical imaging apparatus comprising:
an image detector that acquires at least two projection images from an imaged object at two different positions in an acquisition geometry;
a first data processor that calculates alignment errors between assumed and actual geometric parameters of the acquisition geometry, the first data processor configured for:
applying a weighting function to the at least two projection images;
after applying the weighting function to the at least two projection images, calculating a minimum of a redundant planes cost function, which is determined by:
a) planes each of which intersects an X-ray source trajectory at at least two points;
b) intersection points between the planes and a detector surface for which source positions are determined; and
c) for which parameters determining the intersection points are used for construction of the redundant planes cost function; and
calculating the actual geometric parameters based on the calculated minimum of the redundant planes cost function; and
a second data processor that calculates parameters of the acquisition geometry for an image reconstruction of a plurality of images.

7. The medical imaging apparatus according to claim 6, further comprising:
an X-ray source that exposes the imaged object with X-rays and moves along a predetermined trajectory including a first position and a second position; and
an X-ray detector that faces the X-ray source and detects X-rays emitted from the X-ray source and transmitted through the object.

8. The medical imaging apparatus according to claim 7, wherein the calculated parameters of the acquisition geometry includes an angle between an actual orientation of an image detector relative to one of the planes that intersects with the at least two points defining the X-ray source trajectory.

9. The medical imaging apparatus according to claim 7, wherein the weighting function is a Gaussian function, and weights of pixel values, or respectively redundant cost function values, are increased from 0 to 1 according to a Gaussian distribution in which $3\sigma=L_1$ and $3\sigma=R_1$, and $L_1$ and $R_1$ are relative widths of an applied truncation filter.

10. The medical imaging apparatus according to claim 7, wherein the weighting function is a sigmoid function, and weights of pixel values, or respectively redundant cost function values, are increased from 0 to 1 according to a sigmoid distribution between 0 and $L_1$ and between $R_1$ and 0, and $L_1$ and $R_1$ are relative widths of an applied truncation filter.

11. The medical imaging apparatus according to claim 7, wherein the weighting function is a linear function, and weights of pixel values, or respectively redundant cost function values, are increased from 0 to 1 according to a linear distribution between 0 and $L_1$ and between $R_1$ and 0, and $L_1$ and $R_1$ are relative widths of an applied truncation filter.

12. The medical imaging apparatus according to claim 6, wherein the calculated parameters of the acquisition geometry includes an angle between an actual orientation of an image detector relative to one of the planes that intersects with the points defining the X-ray source trajectory.

13. The medical imaging apparatus according to claim 6, wherein the weighting function is a Gaussian function, and weights of pixel values, or respectively redundant cost function values, are increased from 0 to 1 according to a Gaussian distribution in which $3\sigma=L_1$ and $3\sigma=R_1$, and $L_1$ and $R_1$ are relative widths of an applied truncation filter.

14. The medical imaging apparatus according to claim 6, wherein the weighting function is a sigmoid function, and weights of pixel values, or respectively redundant cost function values, are increased from 0 to 1 according to a sigmoid distribution between 0 and $L_1$ and between $R_1$ and 0, and $L_1$ and $R_1$ are relative widths of an applied truncation filter.

15. The medical imaging apparatus according to claim 6, wherein the weighting function is a linear function, and weights of pixel values, or respectively redundant cost function values, are increased from 0 to 1 according to a linear distribution between 0 and $L_1$ and between $R_1$ and 0, and $L_1$ and $R_1$ are relative widths of an applied truncation filter.

* * * * *